United States Patent [19]

Cobb

[11] 4,334,115

[45] Jun. 8, 1982

[54] PROCESS FOR MAKING TERT-BUTYLTOLUENES

[75] Inventor: Raymond L. Cobb, Bartlesville, Okla.

[73] Assignee: Phillips Petroleum Company, Bartlesville, Okla.

[21] Appl. No.: 274,982

[22] Filed: Jun. 18, 1981

[51] Int. Cl.$^3$ ............................................. C07C 15/395
[52] U.S. Cl. ................................... 585/407; 585/723; 585/415
[58] Field of Search .............. 585/407, 701, 703, 723, 585/14, 16

[56] References Cited

U.S. PATENT DOCUMENTS

| | | | |
|---|---|---|---|
| 2,384,294 | 9/1945 | Frey | 585/703 |
| 2,403,501 | 7/1946 | Clarke | 585/16 |
| 2,467,731 | 4/1949 | Dart et al. | 585/701 |
| 2,758,960 | 8/1956 | Kelly et al. | 585/13 |
| 3,919,343 | 11/1975 | Sabel et al. | 598/23 D F |
| 4,029,716 | 1/1977 | Kaeding | 585/471 |
| 4,080,395 | 3/1978 | Butter | 585/407 |
| 4,169,865 | 10/1979 | Bamforth et al. | 585/314 |
| 4,191,637 | 3/1980 | Light et al. | 208/139 |
| 4,247,726 | 1/1981 | Sleugh | 585/407 |

*Primary Examiner*—Thomas A. Waltz
*Assistant Examiner*—A. Pal

[57] ABSTRACT

A process for obtaining at least one tert-butyltoluene comprising reacting isobutylene and isobutane in the presence of hydrogen fluoride and then separating said toluene from the hydrocarbon product.

6 Claims, No Drawings

PROCESS FOR MAKING TERT-BUTYLTOLUENES

BACKGROUND OF INVENTION

The present invention relates to the production of aromatic compounds from low molecular weight aliphatic compounds. More specifically the present invention relates to the preparation of 4-tert-butyltoluene (TBT) and 3,5-di-tert-butyltoluene (DTBT) from a mixture of isobutane and isobutylene.

Tert-butyltoluenes are valuable chemical intermediates. For example, 4-tert-butyltoluene is employed in large amounts as an intermediate in the fragrance and insecticide industries. Typically, the tert-butyltoluenes have been prepared by processes involving the alkylation of toluene.

An object of the present invention is to provide a means of obtaining tert-butyltoluenes from aliphatic compounds that are often available in greater quantities than aromatic compounds suitable for producing such products.

SUMMARY OF THE INVENTION

In accordance with the present invention, there is provided a method for producing at least one tert-butyltoluene selected from the group consisting of 4-tert-butyltoluene and 3,5-di-tert-butyltoluene comprising reacting a hydrocarbon feed comprising isobutylene and isobutane in the liquid phase in a reaction zone in the presence of liquid hydrogen fluoride under suitable conditions, separating the acid from the hydrocarbon product, and then separating at least one of said tert-butyltoluenes from the hydrocarbon product.

DETAILED DESCRIPTION OF THE INVENTION

The reaction between the isobutane and the isobutylene is carried out using conditions such as those typically used in the HF alkylation of olefins with paraffins.

Generally, the volume ratio of the isobutane to the isobutene is in the range of about 1:1 to about 20:1, more preferably about 2:1 to 8:1. The maximum observed yields of tert-butyltoluenes have been obtained using a volume ratio of isobutane to isobutene of about 4:1. The higher alkane to olefin ratios generally result in increases in the amount of di-tert-butyl-toluene relative to the mono-tert-butyl-toluene.

The HF can be employed in a substantially anhydrous form or in forms diluted with water. In fact, water diluted HF has been noted to often result in even greater levels of aromatic products. A typical diluted HF reactant would contain about 2 weight percent water.

Preferably, the hydrocarbon feedstream that is used in the present invention is free of any substantial amounts of other olefins and paraffins. The addition of other olefins and paraffins has been noted to have a retarding effect upon aromatics production.

The volume ratio of hydrofluoric acid to hydrocarbon feed is generally in the range of about 1:1 to about 20:1, more preferably about 3:1 to 10:1. Generally the yield of the DTBT is increased by increasing the acid to feed ratio and the yield of the TBT is increased by decreasing the acid to feed ratio.

The temperature and pressure are not considered critical. Generally temperatures in the range of 10° C. to 100° C. are suitable, 15° C. to 35° C. being preferred. A pressure is employed sufficient to keep substantially all the reactants and the HF in the liquid phase at the reaction temperature. Typically, it has been noted that the yield of aromatics is lower for longer reaction times.

The liquid products obtained in accordance with the present invention surprisingly contain only trace amounts of other aromatic compounds. Accordingly, the specified products can be separated quite easily in relatively pure form.

The invention and its advantages will be further illustrated by the following examples:

EXAMPLE I

A series of runs were made employing different isoparaffins and isoolefins. The runs were made in the following manner:

To a 2-liter stirred autoclave was added 500 milliliters of anhydrous liquid HF, the stirrer started, and 100 milliliters of a hydrocarbon mixture comprised of 80 milliliters of isobutane and 20 milliliters of isobutene was pressured rapidly into the acid at about 16° C. (60° F.). The reaction mixture was stirred for one minute, and the product mixture pressured immediately into a Jerguson gauge used as a phase separator. The separated acid layer was transferred to an acid recovery cylinder and the hydrocarbon phase was cautiously drained into crushed ice in a separatory funnel, and then washed again with ice-cold water. GLC analyses were run directly on the washed product using a 10 foot×0.25 inch column packed with 5 weight percent SP 1200 and 1.75 weight percent Bentone 34 on Supelcoport (a low polarity ester type material from Supelco, Inc.) programmed from 100°–200° C. at 8° C./minute. No attempt was made to retain light materials during the run. The liquid product recovered was generally in the range of about 20 to 25 weight percent of the total hydrocarbon reactants. The various reactants and the results are set forth in the following Table:

TABLE I

Effect of Alkane-Alkene Type
(Contact Time, 1 minute/HF:Hydrocarbon Vol. Ratio, 5:1)

| Run No. | Hydrocarbon Isoparaffin | Hydrocarbon Isoalkene | Vol. Ratio[a] | % Product by GLC $C_5$-$C_{10}$ | TBT[b] | DTBT[c] |
|---|---|---|---|---|---|---|
| 1 | $C_4$ | $C_4$ | 4:1 | 67 | 10 | 23 |
| 2 | $C_5$ | $C_4$ | 4:1 | 93 | — | 5 |
| 3 | $C_6$ | $C_4$ | 2:1 | 93 | 1 | 1 |
| 4 | $C_4$ | $C_5$ | 2:1 | 92 | 1 | 2 |
| 5 | $C_6$ | $C_5$ | 8:1 | 99 | — | — |

[a]Volume of isoparaffin:volume of isoalkene
[b]Tertiary butyltoluene
[c]Ditertiary butyltoluene The results show that the tert-butyltoluene production is fairly specific to the isobutene and isobutene reactants.

EXAMPLE II

This example compares additional inventive runs wherein the volume ratio of isobutene:isobutene is varied from 2:1 to 8:1. The procedure described in Example I was repeated using the various volumes and the results are shown in Table II wherein the most satisfactory ratio appears to be about 4:1.

TABLE II

Effect of Reactant Volume Ratio
(Contact Time, 1 minute/HF:Hydrocarbon Vol. Ratio, 5:1)

| Run No. | Hydrocarbon Isoparaffin | Isoalkene | Vol. Ratio[a] | % Product by GLC $C_5$–$C_{10}$ | TBT[b] | DTBT[c] |
|---|---|---|---|---|---|---|
| 6 | $C_4$ | $C_4$ | 2:1 | 80 | 6 | 14 |
| 7 | $C_4$ | $C_4$ | 4:1 | 67 | 10 | 23 |
| 8 | $C_4$ | $C_4$ | 6:1 | 83 | 4 | 13 |
| 9 | $C_4$ | $C_4$ | 8:1 | 73 | 5 | 22 |

[a]Volume of isoparaffin:volume of isoalkene
[b]Tertiary butyltoluene
[c]Ditertiary butyltoluene

EXAMPLE III

This example describes inventive runs wherein the contact time of the hydrocarbon mixture and the HF acid solvent is varied from 1 minute to 120 minutes. The procedure described in Example I was repeated at the various contact times and the results are shown in Table III wherein the most satisfactory contact times appear to be short ones, generally less than about 5 minutes.

TABLE III

Effect of Contact Time
(HF:Hydrocarbon Vol. Ratio, 5:1)

| Run No. | Hydrocarbon Isoparaffin | Iso-alkene | Vol. Ratio[a] | Contact Minutes | % Product by GLC $C_5$–$C_{10}$ | TBT[b] | DTBC[c] |
|---|---|---|---|---|---|---|---|
| 10 | $C_4$ | $C_4$ | 2:1 | 1 | 80 | 6 | 14 |
| 11 | $C_4$ | $C_4$ | 2:1 | 2 | 81 | 2 | 17 |
| 12 | $C_4$ | $C_4$ | 2:1 | 3 | 81 | 3 | 16 |
| 13 | $C_4$ | $C_4$ | 2:1 | 20 | 85 | 1 | 14 |
| 14 | $C_4$ | $C_4$ | 2:1 | 60 | 89 | 1 | 10 |
| 15 | $C_4$ | $C_4$ | 2:1 | 120 | 84 | 1 | 11 |

[a]Volume of isoparaffin:volume of isoalkene
[b]Tertiary butyltoluene
[c]Ditertiary butyltoluene

EXAMPLE IV

This example described inventive runs wherein the volume ratio of HF acid-solvent:hydrocarbon feed is varied from 2.5:1 to 10:1. The procedure described in Example I was repeated at the various HF:hydrocarbon (HC) ratios and the results are shown in Table IV wherein it appears that low HF:HC volume ratios (e.g. 2.5:1) favors the formation of tertiary butyltoluene and higher HF:HC volume ratios (e.g. 10:1) favor the formation of ditertiary-butyltoluene.

TABLE IV

Effect of HF:HC Volume Ratios
(Contact Time = 1 minute)

| Run No. | Hydrocarbon Isoparaffin | Iso-alkene | Vol. Ratio[a] | HF:HC Vol. Ratio | % Product by GLC $C_5$–$C_{10}$ | TBT[b] | DTBC[c] |
|---|---|---|---|---|---|---|---|
| 16 | $C_4$ | $C_4$ | 6:1 | 2.5:1 | 75 | 14 | 8 |
| 17 | $C_4$ | $C_4$ | 6:1 | 5:1 | 83 | 4 | 13 |
| 18 | $C_4$ | $C_4$ | 6:1 | 10:1 | 64 | 2 | 32 |

[a]Volume of isoparaffin:volume of isoalkene
[b]Tertiary of butyltoluene [c]Ditertiary butyltoluene

EXAMPLE V

The liquid products from a series of inventive runs were combined, washed with caustic, and distilled through a spinning band column. After the bulk of the material was removed at atmospheric pressure, distillation was continued under vacuum to yield a first fraction having a boiling point around 80° C. at 50 mm Hg and a second fraction having a boiling point around 100° C. at 30 mm Hg. Spectral data (IR and NMR) for the two fractions were substantially the same as those of 4-tert-butyltoluene and 3,5-di-tert-butyltoluene respectively that were prepared by more conventional techniques.

Obviously, variations and modifications of this invention can be made by those skilled in the art without departing from the spirit and scope of the present claims.

What is claimed is:

1. A process for obtaining at least one tert-butyltoluene selected from the group consisting of 4-tert-butyltoluene and 3,5-di-tert-butyltoluene comprising reacting a hydrocarbon feed comprising isobutylene and isobutene in the liquid phase in a reaction zone in the presence of liquid hydrocarbon fluoride under conditions suitable for producing at least one of said tert-butyltoluenes, separating the acid from the hydrocarbon product, and separating at least one of said tert-butyltoluenes from the hydrocarbon product.

2. A process according to claim 1 wherein the volume ratio of said isobutane to said isobutylene is in the range of about 1/1 to about 20/1, the volume ratio of said hydrogen fluoride to said hydrocarbon feed is in the range of about 1/1 to about 20/1, and the temperature of the reaction is in the range of about 10° F. to about 100° F.

3. A process according to claim 2 wherein said hydrocarbon feed is free of any substantial amounts of other olefins or paraffins.

4. A process according to claim 3 wherein the volume ratio of said isobutane to said isobutylene is in the range of about 2/1 to about 8/1, the volume ratio of said hydrogen fluoride to said hydrocarbon feed is in the range of about 3/1 to about 10/1, and the temperature is in the range of about 15° C. to about 35° C.

5. A process according to claims 2 to 4 wherein said hydrogen fluoride contains about 2 weight percent water.

6. A process according to claims 2 to 4 wherein said hydrogen fluoride is substantially anhydrous.

* * * * *

UNITED STATES PATENT AND TRADEMARK OFFICE
CERTIFICATE OF CORRECTION

PATENT NO. : 4,334,115

DATED : June 8, 1982

INVENTOR(S) : Raymond L. Cobb

It is certified that error appears in the above-identified patent and that said Letters Patent are hereby corrected as shown below:

Column 4, line 38, delete "hydrocarbon" and insert therefor --- hydrogen ---.

Signed and Sealed this

Thirty-first Day of August 1982

[SEAL]

Attest:

GERALD J. MOSSINGHOFF

Attesting Officer     Commissioner of Patents and Trademarks